United States Patent
Kitamura et al.

(10) Patent No.: US 9,675,547 B2
(45) Date of Patent: Jun. 13, 2017

(54) LOCAL ADMINISTRATION-TYPE PHARMACEUTICAL FOR IMPROVING DYSPHAGIA

(71) Applicants: Koichi Kitamura, Kanagawa (JP); Maho Kondo, Kanagawa (JP); Kiyoshi Shimoyama, Kanagawa (JP); Toru Kurosawa, Kanagawa (JP)

(72) Inventors: Koichi Kitamura, Kanagawa (JP); Maho Kondo, Kanagawa (JP); Kiyoshi Shimoyama, Kanagawa (JP); Toru Kurosawa, Kanagawa (JP)

(73) Assignee: Meiji Seika Pharma Co., Ltd., Tokyo (JP)

(*) Notice: Subject to any disclaimer, the term of this patent is extended or adjusted under 35 U.S.C. 154(b) by 0 days.

(21) Appl. No.: 14/367,755

(22) PCT Filed: Dec. 20, 2012

(86) PCT No.: PCT/JP2012/083062
§ 371 (c)(1),
(2) Date: Jun. 20, 2014

(87) PCT Pub. No.: WO2013/094682
PCT Pub. Date: Jun. 27, 2013

(65) Prior Publication Data
US 2015/0297512 A1    Oct. 22, 2015

(30) Foreign Application Priority Data
Dec. 21, 2011   (JP) .................... 2011-280365

(51) Int. Cl.
*A61K 31/40*     (2006.01)
*A61K 9/00*      (2006.01)
*A61K 31/401*    (2006.01)

(52) U.S. Cl.
CPC ............ *A61K 9/0053* (2013.01); *A61K 9/006* (2013.01); *A61K 31/40* (2013.01); *A61K 31/401* (2013.01)

(58) Field of Classification Search
CPC ...... A61K 9/0053; A61K 9/006; A61K 31/40; A61K 31/401
(Continued)

(56) References Cited

U.S. PATENT DOCUMENTS

2004/0171669 A1    9/2004  Chenevier
2007/0196495 A1*   8/2007  Soltero ............... A61K 9/0056
                                                        424/488
2010/0316709 A1    12/2010 Kurasawa et al.

FOREIGN PATENT DOCUMENTS

CN    1507347 A    6/2004
CN    1511542   *  7/2004
(Continued)

OTHER PUBLICATIONS

Ishizuka et al ,Cough Syncope Treated with Imidapril in an Elderly Patient with Dysphagia, Chest , 118, 1, Jul. 2000, p. 279.*
(Continued)

*Primary Examiner* — T. Victor Oh
(74) *Attorney, Agent, or Firm* — Foley & Lardner LLP (57) ABSTRACT

A dysphagia improving composition characterized in that a substance having an inhibitory action on an angiotensin converting enzyme, which is a degrading enzyme of substance P, is administered locally in a dosage not influencing blood pressure, and a pharmaceutical for improving dysphagia containing the composition.

10 Claims, 8 Drawing Sheets n=8
***; p< 0.001

(58) Field of Classification Search
USPC .......................................................... 514/423
See application file for complete search history.

(56) References Cited

FOREIGN PATENT DOCUMENTS

| JP | 2004-107285 A | 4/2004 |
|---|---|---|
| JP | 2004-300403 A | 10/2004 |
| JP | 2006-511617 A | 4/2006 |
| JP | 2008-530233 A | 8/2008 |
| JP | 2011-510963 A | 4/2011 |
| WO | WO 2004/054556 A1 | 7/2004 |
| WO | WO 2004/058301 A1 | 7/2004 |
| WO | WO 2006/089082 A2 | 8/2006 |
| WO | WO 2008/081891 A1 | 7/2008 |
| WO | WO 2009/095681 A2 | 8/2009 |
| WO | WO 2010/131486 A1 | 11/2010 |

OTHER PUBLICATIONS

Nakayama et al, ACE inhibitor and Swallowing Reflex, Chest, 113, 5, 1998, p. 1425.*
Teramoto et al., "ACE inhibitors prevent aspiration pneumonia in Asian, but not Caucasian, elderly patients with stroke," European Respiratory Journal, 2007, 29(1):218-219.
Teramoto et al., "ACE inhibitors and prevention of aspiration pneumonia in elderly hypertensives," The Lancet, Mar. 6, 1999, 353:843.
Van de Garde et al., "Angiotensin-converting enzyme inhibitor use and pneumonia risk in a general population," Eur. Respir. J., 2006, 27(6):1217-1222.
Narang et al., "Sublingual Mucosa as a Route for Systemic Drug Delivery," International Journal of Pharmacy and Pharmaceutical Sciences, Mar. 2011, 3(Supp.2):18-22.
Takashi, Ohrui, "Novel strategies for preventing aspiration pneumonia in the elderly," Proceedings of the 52$^{nd}$ Academic Meeting of Japanese Geriatrics Society, Japanese Journal of Geriatrics, 2010, 47:558-560, with English translation.
Chinese Office Action dated Jul. 28, 2015, in CN 201280070003.1.
Supplementary European Search Report dated Sep. 9, 2015, in EP 12859657.4.
Shimizu et al., "ACE inhibitor and swallowing difficulties in stroke, A Preliminary Study," Journal of Neurology, Feb. 21, 2008, 255(2):288-289.
Non-final Office Action dated Jan. 5, 2017, in copending U.S. Appl. No. 14/897,317.
Ardekani et al., "Topical Captopril as a Novel Agent Against Hypertrophic Scar Formation in New Zealand White Rabbit Skin," Wounds: A Compendium of Clinical Research and Practice, May 2008, 20(5):Article 8587, 10 pages.
Ardekani et al., "Treatment of a Postburn Keloid Scar with Topical Captopril: Report of the First Case," Plastic and Reconstructive Surgery, Feb. 2009, 123(3):112e-113e.
Brown et al., "Angiotensin-Converting Enzyme Inhibitors," Circulation, 1998, 97:1411-1420.

* cited by examiner

LOCAL ADMINISTRATION-TYPE PHARMACEUTICAL FOR IMPROVING DYSPHAGIA

CROSS-REFERENCE TO RELATED APPLICATIONS

This application is a National Stage application of PCT/JP2012/083062, filed Dec. 20, 2012, which claims priority from Japanese application JP 2011-280365, filed Dec. 21, 2011.

TECHNICAL FIELD

The present invention relates to a pharmaceutical composition for improvement of dysphagia and prevention of aspiration pneumonia.

BACKGROUND ART

In the case of dysphagia, swallowing becomes difficult in eating and drinking, and a patient is often forced to give up eating and drinking through the mouth, nutrition intake, which raises a great problem from the viewpoint of QOL. At the same time, mental and physical stress on a caregiver who cares for eating and drinking becomes very heavy. Further, the percentage of pneumonia in causes of death in the elderly increases sharply, and a most part thereof is believed to be aspiration pneumonia caused by dysphagia.

Onset of dysphagia is frequently caused by disorder of basal ganglia derived from cerebral vascular disorder, Parkinson's disease, aging, excessive administration of an antipsychotic drug, or the like. By reduced activity of the nigrostriatal dopaminergic neurons in the site, synthesis of substance P, which is up-regulated by dopaminergic neurons, is decreased. When the synthesized substance P is released from a nerve terminal of the vagal nerve and the glossopharyngeal nerve sensory branch, a swallowing reflex is elicited. Therefore, decrease in the amount of substance P decreases a swallowing reflex to trigger aspiration, and especially when intraoral bacteria enter into the lung by inapparent aspiration, they can cause aspiration pneumonia. Consequently, improvement of a swallowing reflex in eating and drinking is quite important for a person inconvenienced by dysphagia to improve their QOL, and for caregiver to reduce the burden, as well as to prevent aspiration pneumonia.

Conventionally, as a treatment method for dysphagia, rehabilitation has been practiced. However, the rehabilitation requires sometimes unreasonable endeavor of a relevant person, and is applicable not to all symptoms. As a treatment using a drug or the like, the following Non-Patent Literature and Patent Literature report as a conventional example that capsaicin, a pungent component, promotes release of substance P from a nerve terminal and improves swallowing reflex (Patent Literature 1), but also report that continuously use of capsaicin induces depletion of substance P. Further, it is suggested that a preparation used for a treatment of Parkinson's disease, such as levodopa and amantadine, improves dysphagia by acting on dopaminergic neurons in the nigrostriatum (Non-Patent Literature 1), but due to side effects administration must be done cautiously. Meanwhile, an angiotensin converting enzyme participates in degradation of angiotensin I as well as substance P as substrates, and therefore it is inferred that by administration of an angiotensin converting enzyme inhibitor degradation of substance P is suppressed and dysphagia can be improved, and further it is reported that onset of pneumonia can be suppressed (Non-Patent Literature 1). However, in order to inhibit the action of an angiotensin converting enzyme by oral administration, an angiotensin converting enzyme inhibitor is used in the same dosage as that used as an antihypertensive agent, and therefore care needs to be taken in using the inhibitor, because the inhibitor decreases the blood pressure of a person with a normal blood pressure or even with a low blood pressure. Especially in the case of an aged person, excessive reduction of the blood pressure may have various negative influences, such as dizziness, lightheadedness, sleeplessness, and fatigue, as well as decrease in an intracerebral blood flow amount.

CITATION LIST

Patent Literature

Patent Literature 1: JP Patent Publication (Kokai) No. 2004-300103A

Non Patent Literature

Non Patent Literature 1: Ohrui Takashi, Status Quo of Aspiration Pneumonia in Elderly and Countermeasures, Proceedings of the 52nd academic meeting of Japanese Geriatrics Society, Japanese Journal of Geriatrics, (2010) 47: 558-560

SUMMARY OF INVENTION

Technical Problem

As described above, past compositions or treatments for prevention of aspiration pneumonia and improvement of dysphagia have inevitably side effects. Therefore, the first object of the present inventors is to develop a pharmaceutical for prevention of aspiration pneumonia and improvement of dysphagia with little side effect. The second object is to develop a pharmaceutical containing an agent having an inhibitory action on an angiotensin converting enzyme as an active ingredient, to be applied by a specific administration method for prevention of aspiration pneumonia and improvement of dysphagia without causing a side effect such as blood pressure reduction. Further, the third object is to develop a pharmaceutical containing an agent having an inhibitory action on an angiotensin converting enzyme as an active ingredient, with which by a specific administration method an improving effect on dysphagia can be seen soon after the administration, though by oral administration the improving effect on dysphagia soon after the administration cannot be expected.

Solution to Problem

Under such circumstances, the present inventors conducted diverse investigations and found that by administering a substance having an inhibitory action on an angiotensin converting enzyme directly to a pharyngeal part a strong improving effect on dysphagia can be obtained without exhibiting a blood-pressure-lowering effect.

A pharmaceutical for improving dysphagia according to the present invention completed based on the above knowledge contains a component having an inhibitory action on an angiotensin converting enzyme to be administered locally to a pharyngeal site as an active ingredient.

A drug for improving dysphagia according to the invention of the present application includes a therapeutic drug for dysphagia, and a preventive agent for dysphagia.

This application claims priority based on Japanese Patent Application No. 2011-280365, the contents of the description and/or drawings of which are incorporated herein by reference.

Advantageous Effects of Invention

The present invention provides a pharmaceutical composition, by which improvement of dysphagia and prevention of aspiration pneumonia can be expected by using a substance having an inhibitory action on an angiotensin converting enzyme with an administration method and a dose, which do not influence the blood pressure. Further, the invention of the present application can improve dysphagia at a time point when oral administration cannot yet develop an effect, namely instantaneously.

DESCRIPTION OF EMBODIMENTS

1. Dysphagia Improving Drug: Substance Having an Inhibitory Action on an Angiotensin Converting Enzyme A substance having an inhibitory action on an angiotensin converting enzyme is an inhibitory substance of an enzyme converting angiotensin I to angiotensin II, and used in general for a treatment of hypertension. An angiotensin converting enzyme has low substrate selectivity and degrades also substance P as a substrate. By administration of a substance having an inhibitory action on an angiotensin converting enzyme for inhibiting degradation of substance P, the concentration of the substance P in the body is increased, and dysphagia can be improved.

Typical examples of a substance having an inhibitory action on an angiotensin converting enzyme herein include captopril, lisinopril, enalapril, benazepril, imidapril, alacepril, perindopril, quinapril, temocapril, trandolapril, cilazapril, and delapril as well as active metabolites thereof 2. Mode of Administration and Administration Route With a dysphagia improving drug containing a substance having an inhibitory action on an angiotensin converting enzyme as an active ingredient according to the invention, the active ingredient can be administered locally. More specifically, a dysphagia improving drug according to the invention includes a dysphagia improving drug, which locally administers a substance having an inhibitory action on an angiotensin converting enzyme as an active ingredient to at least one site selected from an intraoral site, a pharyngeal site, a laryngeal site and the respiratory tract. By local administration to at least one site selected from an intraoral site, a pharyngeal site, a laryngeal site and the respiratory tract as above, dysphagia can be improved by a substance having an inhibitory action on an angiotensin converting enzyme without exhibiting a blood-pressure-lowering effect, thereby preventing aspiration pneumonia.

More favorably, a dysphagia improving drug according to the invention includes a dysphagia improving drug, which locally administers a substance having an inhibitory action on an angiotensin converting enzyme as an active ingredient to a pharyngeal site. The local administration can be made, for example, in a mode by which the drug is directly applied to the pharyngeal mucosa.

3. Dosage Form

A dysphagia improving drug according to the invention is applied in a form to be absorbed by the intraoral mucosa, the pharyngolaryngeal mucosa, and the respiratory tract mucosa. More specifically, it may be in the form of a spray, a film preparation, an oral/endolaryngeal patch, a nebulizer, a liquid for direct application or the like, containing a substance having an inhibitory action on an angiotensin converting enzyme as an active ingredient.

(1) Examples of an edible and water-soluble film base to be used for a film preparation or an oral/endolaryngeal patch include gelatin, pectin, arabinoxylan, sodium alginate, carrageenan, xanthan gum, guar gum, pullulan, hypromellose, hydroxypropyl cellulose, water-soluble hydroxyethyl cellulose, methyl cellulose, carboxymethyl cellulose, polyvinyl alcohol, polyvinylpyrrolidone, and polyethylene glycol.

(2) As a carrier to be used for an inhalant (nebulizer) or a spray, a saccharide, a sugar alcohol, an amino acid and/or an inorganic salt can be used. Examples of a saccharide include milk sugar, grape sugar, cane sugar, maltose, trehalose, maltodextrin, and dextran. Examples of a sugar alcohol include mannitol, xylitol, erythritol, maltitol, sorbitol, arabitol, and xylose. Examples of an amino acid include leucine, isoleucine, lysine, valine, threonine, methionine, cysteine, cystine, phenyl alanine, tryptophan, and glycine. Examples of an inorganic salt include calcium carbonate, sodium chloride, and calcium phosphate. Milk sugar may be used favorably.

(3) To a liquid for direct application, an emulsifier, a suspending agent, or a preservative may be added as needed. Examples of an emulsifier include polysorbate 80, lauromacrogol, glyceryl monostearate, sodium lauryl sulfate, and lecithin. Examples of a suspending agent include polyvinyl alcohol, povidone, carmellose sodium, methyl cellulose, hydroxypropyl cellulose, hydroxyethyl cellulose, sodium alginate, and gum arabic.

4. Administration Target

A dysphagia improving drug according to the invention may be administered to a dysphagia patient, and an aged person, a patient with cerebral vascular disorder, a Parkinson's disease patient, and a person taking an antipsychotic drug, who are susceptible to dysphagia.

Since spraying, nebulizing, or direct application is an administration method not demanding a swallowing work of saliva, it can be applied irrespective of the degree of swallowing function disorder. Therefore, administration by spraying, nebulizing, or direct application is preferable in the case of severe dysphagia.

5. Timing and Frequency of Administrations

A dysphagia improving drug according to the invention may be administered locally 1 to several times per day to an intraoral site, a pharyngeal site, a laryngeal site and/or the respiratory tract. In this regard, according to the invention, dysphagia can be improved within a period, in which an oral administration does not yet develop an effect. In other words, the administration works rapidly, and therefore an inhibitory component of an angiotensin converting enzyme can be favorably applied directly to the pharyngeal mucosa, for example, before every meal and/or before bedtime.

The invention will now be described in more detail by way of Examples, etc., provided that the following description should not be considered to limit the scope of the invention in any way.

It has been known as described above, that dysphagia derived from basal ganglia disorder may appear due to administration of an antipsychotic drug, such as haloperidol, which suppresses the action of dopaminergic neurons. Therefore the inventors constructed an animal model of swallowing function disorder induced by repeated overdosage of haloperidol, and evaluated the drug efficacy.

Experimental Example 1

To 6 week-old female Hartley guinea pigs (330 to 390 g) habituated for 1 week after receipt, a physiological saline solution, or a haloperidol solution was injected subcutaneously in a dosage of 1 mg/kg approx. every 12 hours twice per day for 7 days. Thereafter, a guinea pig was fixed at extremities, and 500 μL of distilled water was injected over 5 sec through a device to a part just before the pharynx, and the total frequency of swallowing until 10 sec and 30 sec from the injection was measured based on a muscle movement in a pharyngeal site. Thereafter a physiological saline solution, or a haloperidol solution was injected again (1 mg/kg).

Result

Figure 1:
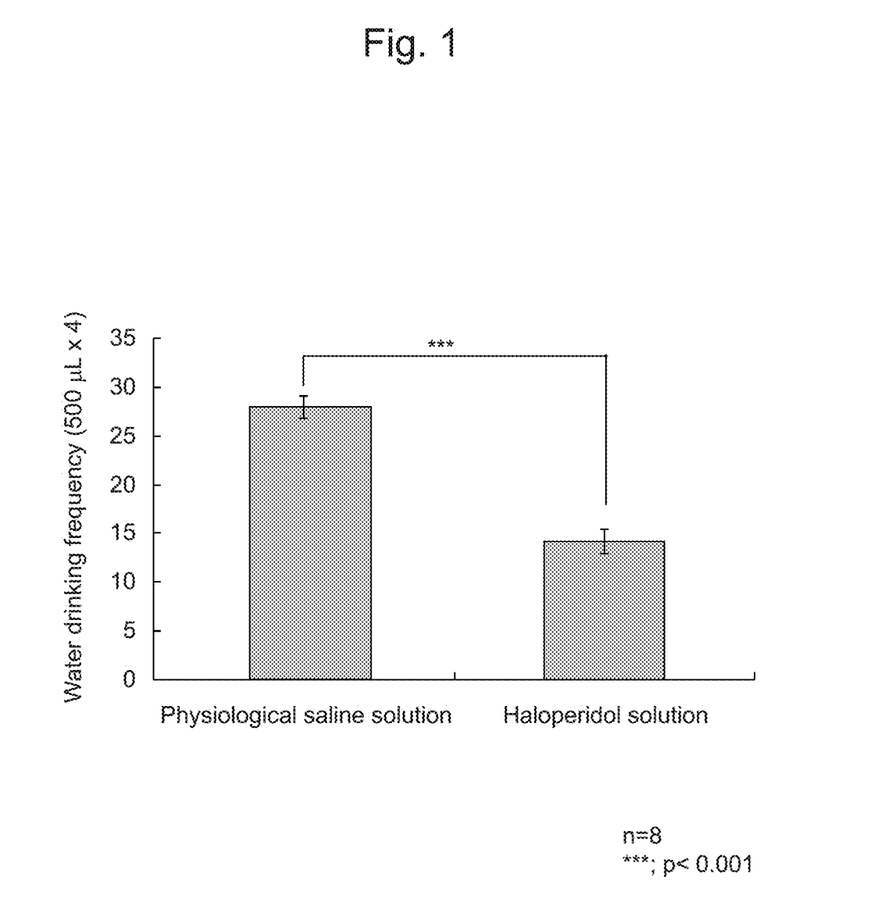
FIG. 1 is a graph showing the results of a study of a swallowing reflex decreasing effect by multiple administrations of haloperidol in Experimental Example 1.

The measurements were repeated totally 4 times at intervals of 1 min. The results are shown in FIG. 1. As obvious from FIG. 1, water drinking frequency in the group received repeated administrations of haloperidol is significantly decreased compared to the guinea pig group received repeated administrations of a physiological saline solution. Based on the result, the guinea pig was used as a dysphagia model induced by repeated administrations of haloperidol in the following experiments for evaluation of drug efficacy.

Example 1

Effect of Captopril Local Administration

In the same way as in Experimental Example 1, 1 mg/kg of a haloperidol solution was administered repeatedly to 6-week old Hartley female guinea pigs (330 to 390 g), and on day 8 water drinking reflection was measured as above, which was defined as an initial value. On day 2 of the initial value measurement, 100 μL of distilled water, or an aqueous solution with 50 mM, 50 μM, or 50 nM of captopril (pH 7.0) was sprayed with a spray device directly to the pharyngeal mucosa of a guinea pig. Water drinking reflection was measured 30 min after the spray in the same way as in the initial value measurement (measured value).

Figure 2:
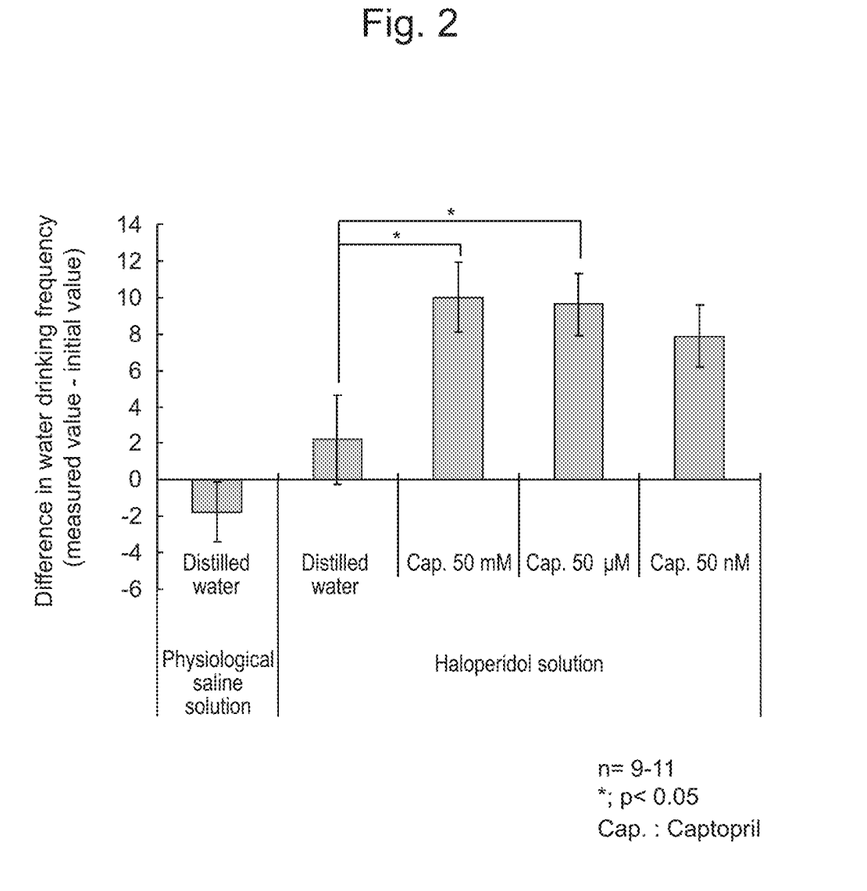
FIG. 2 is a graph showing the results of a study of a swallowing reflex improving effect by local administration to a pharyngeal site of a captopril aqueous solution in a guinea pig dysphagia model received multiple administrations of haloperidol in Example 1.

The results are shown in FIG. 2. As obvious from FIG. 2, there was no significant change in the water drinking frequency in the group sprayed with distilled water, but significant increase in the water drinking frequency was observed in the groups sprayed with aqueous solutions containing 50 mM or 50 μM of captopril.

Example 2

Effect of Lisinopril Local Administration

A guinea pig dysphagia model induced by repeated administrations of haloperidol was prepared in the same way as in Example 1, and 100 μL of a 0.5 nM to 500 μM aqueous solution of lisinopril (pH 7.0) was sprayed with a spray device directly to the pharyngeal mucosa of a guinea pig, followed by measurement of the influence on water drinking reflection.

Figure 3:
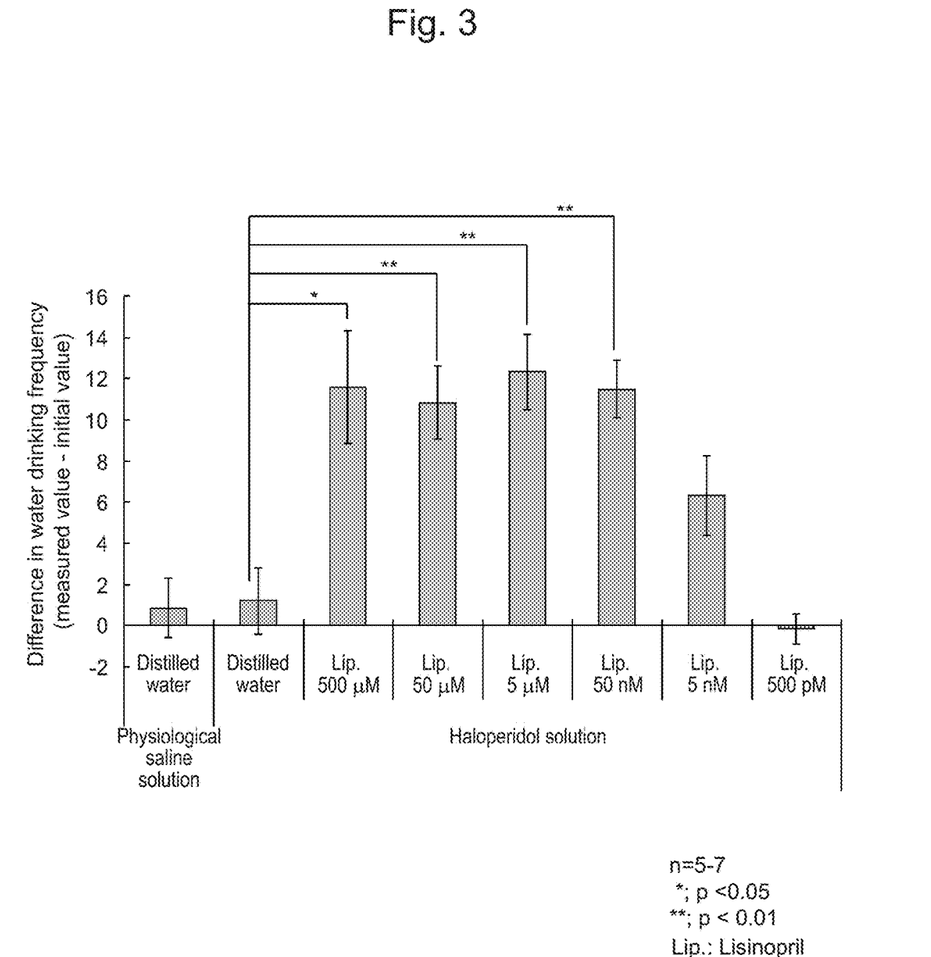
FIG. 3 is a graph showing the results of a study of a swallowing reflex improving effect by local administration to a pharyngeal site of a lisinopril aqueous solution in a guinea pig dysphagia model received multiple administrations of haloperidol in Example 2.

The results are shown in FIG. 3. As obvious from FIG. 3, there was no significant change in water drinking frequency in the group sprayed with distilled water, but dose-dependent increase in water drinking frequency was observed in the groups sprayed with a lisinopril aqueous solution, and at a dose of 50 nM or more there was significant increase in water drinking frequency in the same way as in the group sprayed with a 50 μM aqueous solution of captopril.

Example 3

Involvement of Substance P, Prevention of Dysphagia

FK888 (10 μM, 50 μL/guinea pig), which is a substance P receptor antagonist, was administered locally with a spray device to a pharyngeal site of a guinea pig, and water drinking reflection frequency was measured in the same way as in Experiment 1.

Figure 4:
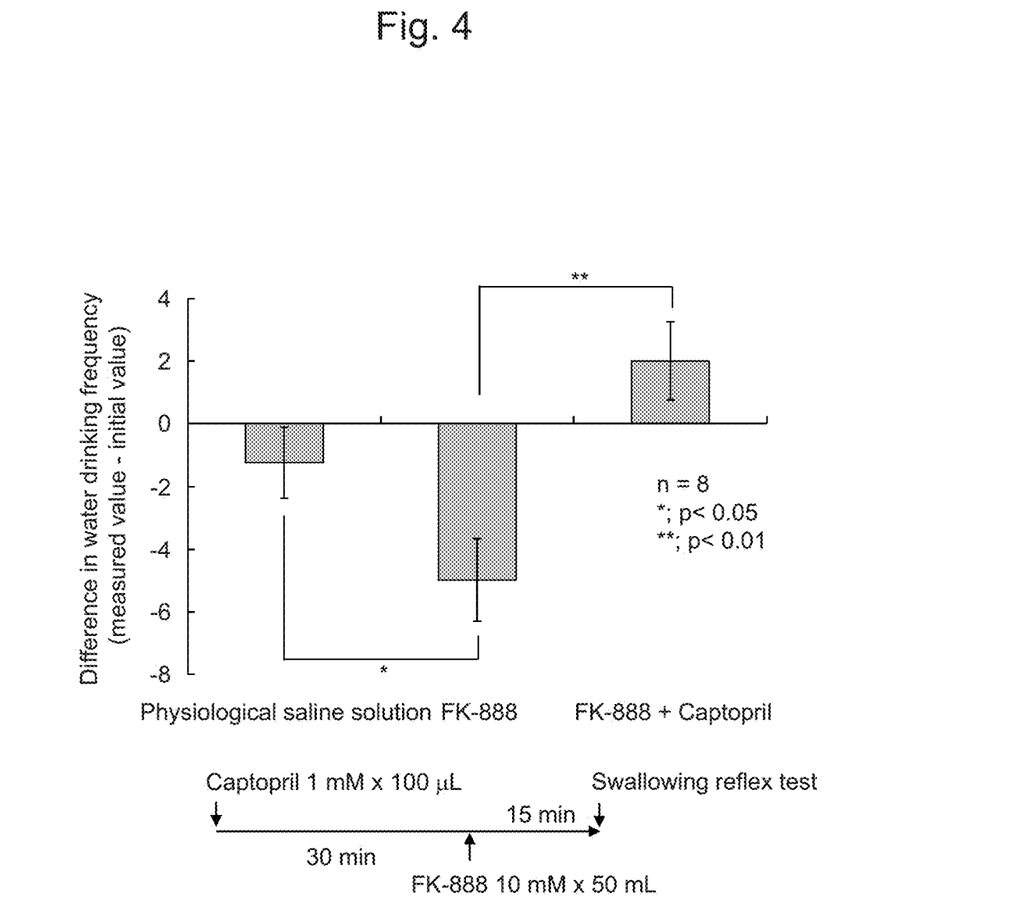
FIG. 4 is a graph showing the results of a study of decrease in a swallowing reflex in a normal guinea pig by local administration to a pharyngeal site of a substance P receptor antagonist, and an improving effect by a prior local administration to the pharyngeal site of a captopril aqueous solution in Example 3.

The results are shown in FIG. 4. As obvious from FIG. 4, decrease in swallowing reflex by local administration to a pharyngeal site of FK888 was observed. Further, in the case, in which an aqueous solution of captopril was administered locally 30 min before the administration of FK888 with a spray device to a pharyngeal site in the same way as in Example 1, decrease in swallowing reflex by the FK888 administration was suppressed.

Example 4

Involvement of Substance P, Mechanism of Dysphagia Improving Effect

A guinea pig dysphagia model induced by repeated administrations of haloperidol was prepared, and 100 µL of a 50 nM aqueous solution of lisinopril was sprayed with a spray device directly to the pharyngeal mucosa. Thereafter, 10 nM, 100 µL of FK888 as a substance P receptor antagonist, which is the lower limit not influencing swallowing reflex, was administered locally with a spray device to the pharyngeal mucosa, and water drinking frequency was measured in the same way as in Experimental Example 1.

Figure 5:
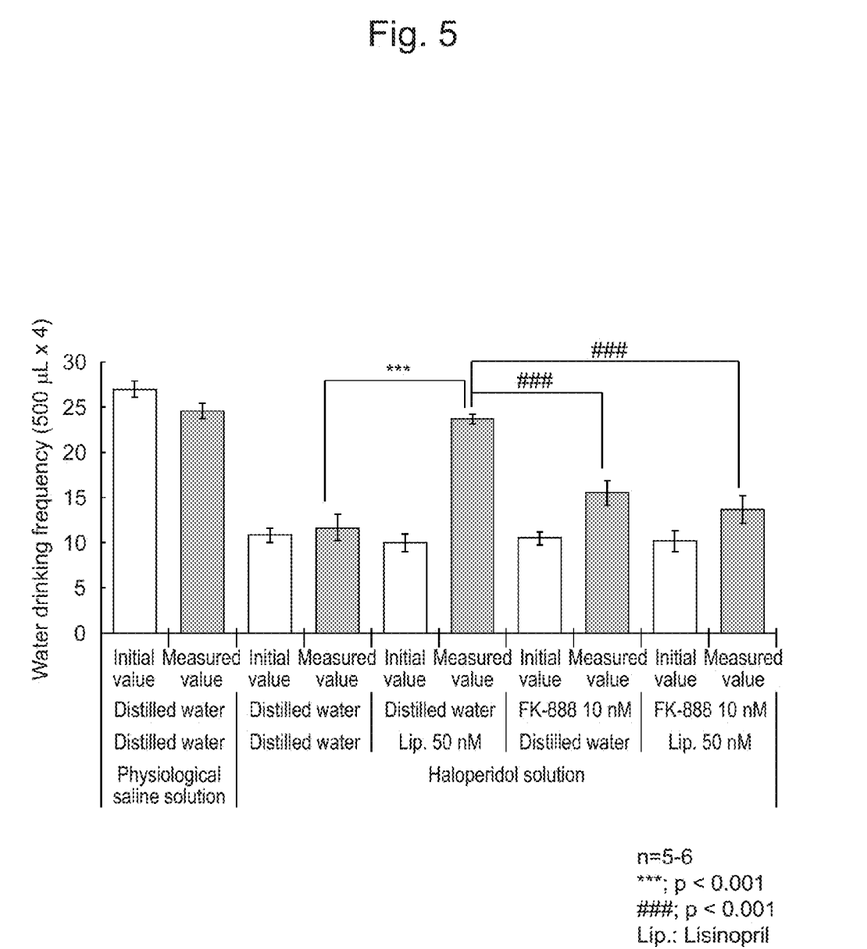
FIG. 5 is a graph showing the results of a study of an effect of local administration to a pharyngeal site of a substance P receptor antagonist on a swallowing reflex improving effect by local administration to a pharyngeal site of a lisinopril aqueous solution in guinea pigs dysphagia model received multiple administrations of haloperidol in Example 4.

The results are shown in FIG. 5. As obvious from FIG. 5, increase in water drinking frequency observed 30 min after the administration of 100 µL of a 50 nM aqueous solution of lisinopril was almost completely suppressed by the administration of FK888 (10 nM, 100 µL) 15 min after the lisinopril administration.

Comparative Example 1

Advantage of Captopril Local Administration

With respect to the dysphagia improving effect by a substance having an inhibitory action on an angiotensin converting enzyme, an oral administration (p.o., intragastric administration) and a local administration with a spray device to the pharyngeal mucosa (s.i.) were compared in terms of change in water drinking frequency. A guinea pig dysphagia model induced by repeated administrations of haloperidol was prepared in the same way as in Example 1, and 100 µL of a 50 µM aqueous solution of captopril, or a 50 mM aqueous solution of captopril was administered locally with a spray device to the pharyngeal mucosa, or the same dose of captopril was administered orally (intragastric administration). The water drinking frequency was measured 30 min after the administration.

Figure 6:
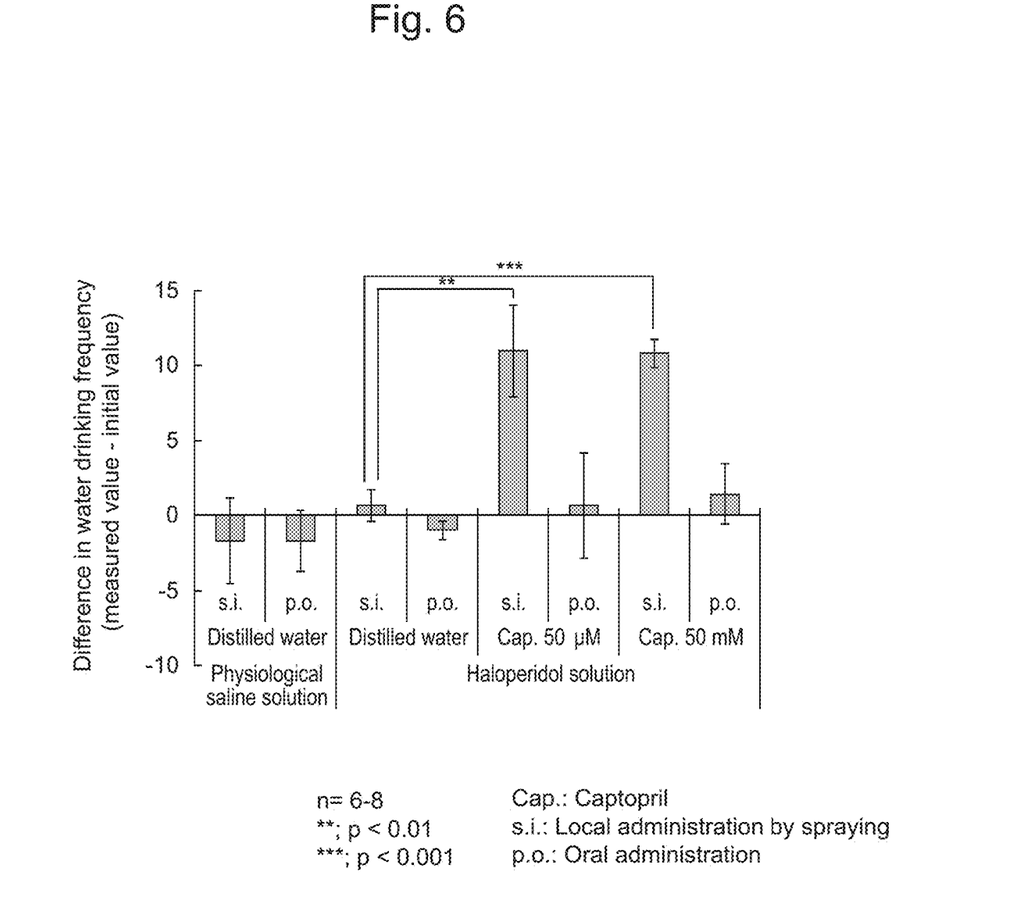
FIG. 6 is a graph showing the results of a study of swallowing reflex improving effects by local administration to a pharyngeal site and oral systemic administration of a captopril aqueous solution after 30 min of the administration in guinea pigs dysphagia model received multiple administrations of haloperidol in Comparative Example 1.

The results are shown in FIG. 6. As obvious from FIG. 6, a local administration of either of the 50 µM captopril aqueous solution and the 50 mM captopril aqueous solution in an amount of 100 µL, exhibited an improving effect on dysphagia within a short time of 30 min from the administration, however an oral administration of either of the dosages did not exert an influence.

Comparative Example 2

Advantage of Lisinopril Local Administration

With respect to the dysphagia improving effect by lisinopril, an oral administration (p.o., intragastric administration) and a local administration to the pharyngeal mucosa (s.i.) were compared in terms of change in water drinking frequency in the same way as in Comparative Example 1. A guinea pig dysphagia model induced by repeated administrations of haloperidol was prepared, and 100 µL of a 50 mM lisinopril aqueous solution was administered locally with a spray device to the pharyngeal mucosa, or the same dose of lisinopril was administered orally (intragastric administration). The water drinking frequency was measured 2 hours after the administration (when the blood drug concentration after an oral administration reaches a maximum).

Figure 7:
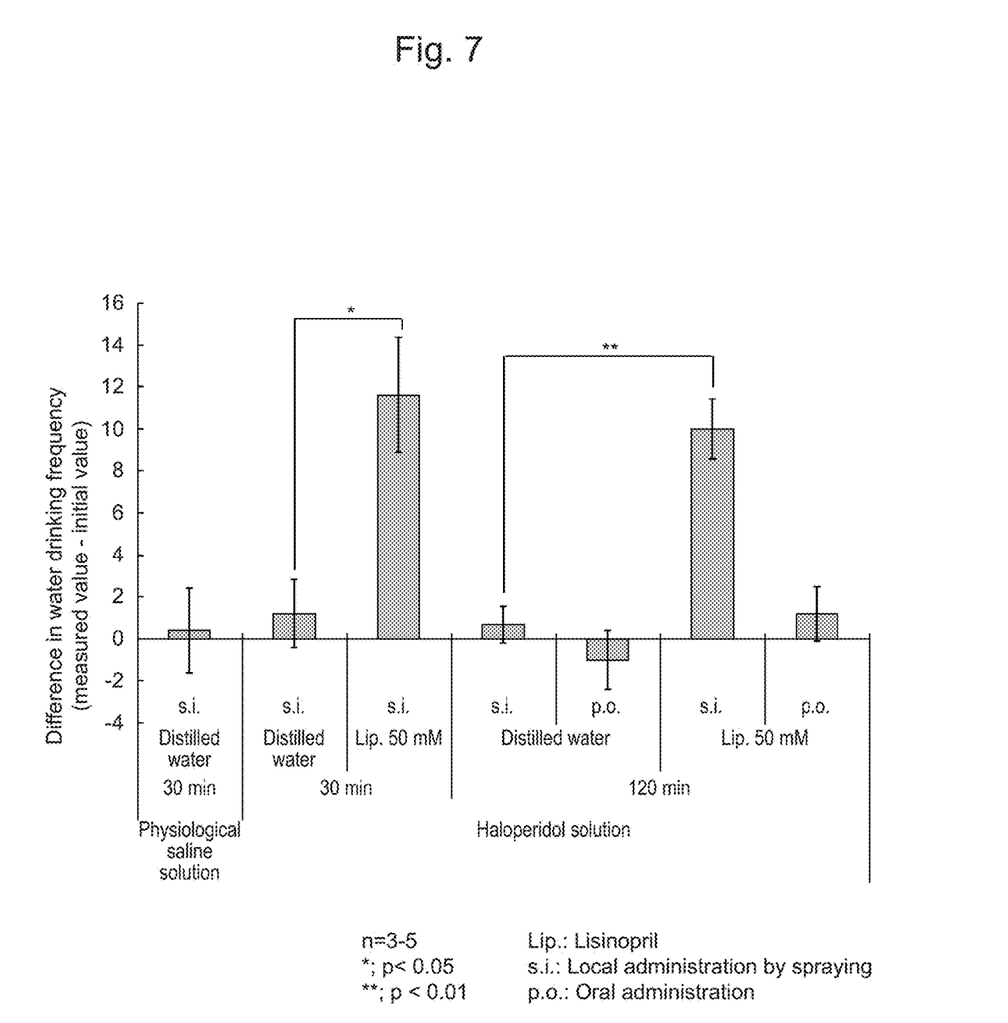
FIG. 7 is a graph showing the results of a study of swallowing reflex improving effects by local administration to a pharyngeal site and oral systemic administration of a lisinopril aqueous solution after 120 min of the administration in a dysphagia model received multiple administrations of haloperidol in Comparative Example 2.

The results are shown in FIG. 7. As obvious from FIG. 7, a local administration of 100 µL of the 50 µM lisinopril aqueous solution exhibited an improving effect on dysphagia even 2 hours after the administration, but an oral administration exerted no influence.

Comparative Example 3

Effect on Blood Pressure Increase Induced by Angiotensin I

Influence of a dose of a 50 µM aqueous solution of captopril in an amount of 100 µL, or a 5 µM aqueous solution of lisinopril in an amount of 100 µL, which exhibited improvement of dysphagia in Example 1 and Example 2, on blood pressure was analyzed using SD male rats (350 to 400 g). The respective dose of a captopril, or lisinopril aqueous solution was administered orally and the blood pressures were measured after 1 hour. Thereafter, angiotensin I was administered intravenously (300 ng/kg) to induce blood pressure increase and a change in the mean blood pressure was measured.

Figure 8:
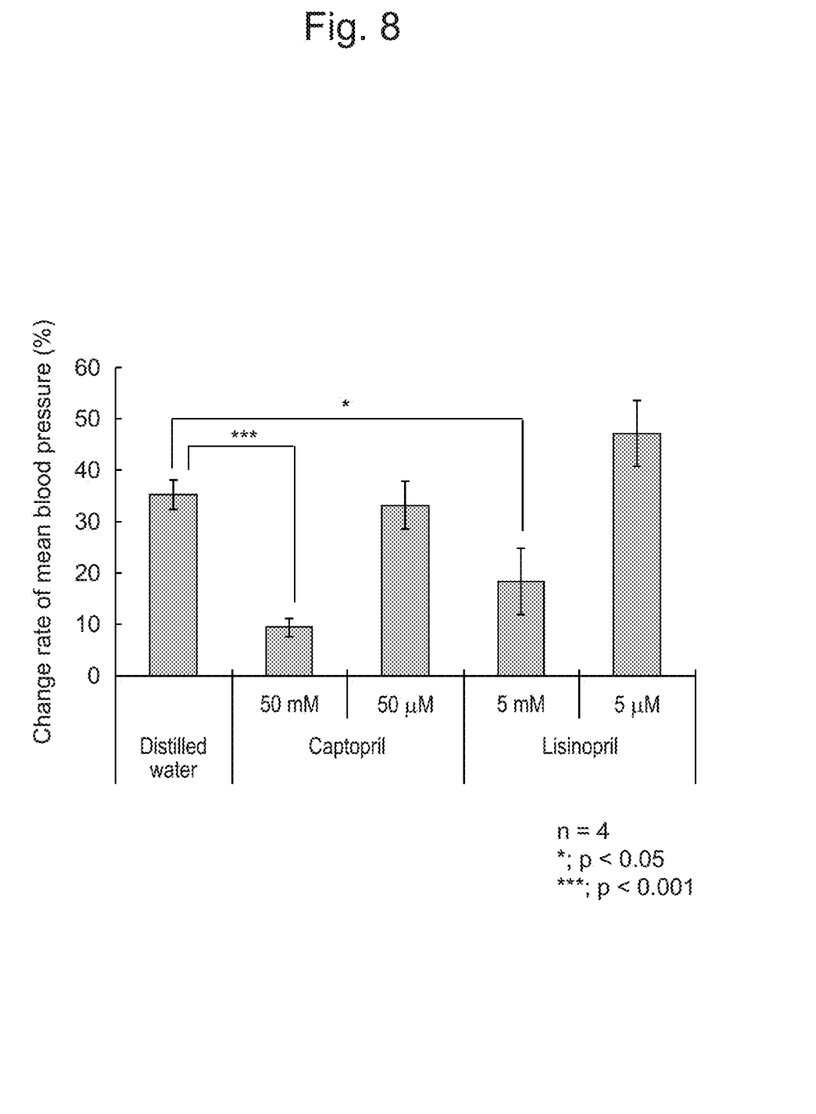
FIG. 8 is a graph showing the results of a study of an influence of a prior administration of a captopril aqueous solution or a lisinopril aqueous solution on blood pressure increase by intravenous administration of angiotensin I in a normal rat in Comparative Example 3.

The results are shown in FIG. 8. As obvious from FIG. 8, administration of 100 µL of the 50 mM aqueous solution of captopril, or 100 µL of the 5 mM aqueous solution of lisinopril suppressed a vasopressor reaction by administration of angiotensin I, but administration of 100 µL of the 50 µM aqueous solution of captopril, or 100 µL of the 5 µM aqueous solution of lisinopril had no influence.

It has been known that overdosage of haloperidol induces also in a human clinical case decrease in an amount of substance P in blood and also decrease in swallowing reflex. Therefore it was so considered that a guinea pig dysphagia model induced by repeated administrations of haloperidol used according to the invention reflected the human clinical status.

From Example 1, Example 2, and Comparative Example 3 it became clear that decrease in swallowing reflex could be improved by local administration of a substance having an inhibitory action on an angiotensin converting enzyme to a pharyngeal site at a dose not affecting the blood pressure.

From Example 3 it could be so understood that a local administration of a substance having an inhibitory action on an angiotensin converting enzyme to a pharyngeal site could suppress prophylactically dysphagia to be caused by a substance P receptor antagonist by suppressing degradation of substance P in pharyngeal tissues. In addition, from Example 4 it could be so understood that a local administration of a substance having an inhibitory action on an angiotensin converting enzyme to a pharyngeal site could improve disorder in a guinea pig dysphagia model induced by repeated administrations of haloperidol by suppressing degradation of substance P in pharyngeal tissues so as to enhance swallowing reflex elicited by substance P.

It was so judged from Example 1, Example 2, Comparative Example 1, Comparative Example 2, and Comparative Example 3 that by local administration of a substance having an inhibitory action on an angiotensin converting enzyme, not only improvement of dysphagia at a low dose, which does not affect the blood pressure, can be achieved, but also an early improving effect on dysphagia, which cannot be obtained by an oral administration, can be obtained. The dose of 100 µL of a 50 mM captopril aqueous solution in Comparative Example 1 is a dose exhibiting an advantageous blood-pressure-lowering effect in various animal models. The dose of 100 µL of a 50 mM lisinopril aqueous solution in Comparative Example 2 is almost equivalent to a human clinical dose based on the body weight as a therapeutic drug for hypertension, and is a dose exhibiting adequate blood-pressure-lowering effect in a human and an animal, but no dysphagia improving effect was observed by an oral administration even at a time point when the blood drug concentration was maximum. It was then judged that oral administration of a dose used for a human clinical treatment of hypertension could not obtain an early improving effect on dysphagia as in the case of a local administration. From the above it has been concluded that a local administration of a substance having an inhibitory action on an angiotensin converting enzyme to a pharyngeal site is a superior application method to provide a dysphagia improving drug, which does not induce depletion of substance P from a nerve terminal, not cause various side effects such as blood pressure decrease as in the case of an oral administration of a dopamine preparation or a substance having an inhibitory action on an angiotensin converting enzyme, and can exhibit drug efficacy early after administration.

All the publications, patents, and patent applications cited herein are incorporated herein in their entirety by reference.

The invention claimed is:

1. A method for treating a subject suffering from dysphagia or aspiration pneumonia, comprising administering to the subject a dysphagia improving drug comprising captopril as an active ingredient at a dosage from 0.65 ng/kg to 650 ng/kg, wherein the drug is administered locally to at least one site selected from an intraoral site, a pharyngolaryngeal site, and the respiratory tract, and wherein the drug improves dysphagia without lowering blood pressure.

2. The method of claim 1, wherein the drug is fast-acting.

3. The method of claim 1, wherein the drug is administered in a liquid form.

4. The method of claim 1, wherein the drug improves dysphagia within a period during which an oral administration does not exert an effect.

5. The method of claim 1, wherein the drug is administered by spray, nebulizer or direct application to pharyngeal mucosa.

6. A method for treating a subject suffering from dysphagia or aspiration pneumonia, comprising administering to the subject a dysphagia improving drug comprising lisinopril as an active ingredient at a dosage from 1.2 ng/kg to 120 ng/kg, wherein the drug is administered locally to at least one site selected from an intraoral site, a pharyngolaryngeal site, and the respiratory tract, and wherein the drug improves dysphagia without lowering blood pressure.

7. The method of claim 6, wherein the drug is fast-acting.

8. The method of claim 6, wherein the drug is administered in a liquid form.

9. The method of claim 6, wherein the drug improves dysphagia within a period during which an oral administration does not exert an effect.

10. The method of claim 6, wherein the drug is administered by spray, nebulizer or direct application to pharyngeal mucosa.

* * * * *